(12) United States Patent
Shade et al.

(10) Patent No.: US 7,005,446 B1
(45) Date of Patent: Feb. 28, 2006

(54) USE OF AP-1 ACTIVATORS TO TREAT GLAUCOMA AND OCULAR HYPERTENSION

(75) Inventors: Debra L. Shade, Benbrook, TX (US); Iok-Hou Pang, Grand Prairie, TX (US); Abbot F. Clark, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/913,098

(22) PCT Filed: Apr. 7, 2000

(86) PCT No.: PCT/US00/09503

§ 371 (c)(1),
(2), (4) Date: Aug. 9, 2001

(87) PCT Pub. No.: WO00/62769

PCT Pub. Date: Oct. 26, 2000

Related U.S. Application Data

(60) Provisional application No. 60/130,133, filed on Apr. 20, 1999.

(51) Int. Cl.
*A61K 31/40* (2006.01)

(52) U.S. Cl. .................. 514/428; 514/408; 514/913

(58) Field of Classification Search ........... 514/408, 514/428, 913
See application file for complete search history.

(56) References Cited

U.S. PATENT DOCUMENTS

| | | | | |
|---|---|---|---|---|
| 4,565,821 | A | * | 1/1986 | Chiou ................ 514/327 |
| 5,637,610 | A | * | 6/1997 | Nakabayashi et al. ...... 514/458 |
| 5,981,568 | A | | 11/1999 | Kunz et al. ............ 514/411 |

FOREIGN PATENT DOCUMENTS

WO    WO 98/01137    1/1998

OTHER PUBLICATIONS

Foletta et al., "Transcriptional regulation in the immune systems: all roads lead to AP-1," *Journal Leukocyte Biology.*, vol. 63:139-152, 1998.

Karin et al., "AP-1 function and regulation," *Current. Opinion in Cell Biology*, vol. 9:240-246, 1997.

Lee et al., "Activation of transcription by two factors that bind promoter and enhancer sequences of the human metallothionein gene and SV40," Nature, vol. 325:368-372, (1987).

Whitmarsh et al., "Transcription factor AP-1 regulation by mitogen-activated protein kinase signal transduction pathways," J. Mol. Med., vol. 74:589-607, 1996.

Ainbinder et al., "Regulatory mechanisms involved in activator-protein-1 (AP-1)-mediated activation of glutathione-S-transferase gene expression by chemical . . . ," Eur. J. Biochem., vol. 243:49-57, 1997.

Xie et al., "ARE- and TRE-mediated regulation of gene expression," *Journal of Biological Chemistry*, vol. 270(12): 6894-6900, 1995.

Ainbinder et al., "Signaling pathways in the induction of c-fos and c-jun proto-oncogenes by 3-methylcholanthrene," *Receptors and Signal Transduction*, vol. 7(4):279-289, 1997.

Oazki et al., "The comparative effects of haloperidol, (-)-sulpiride, and SCH23390 on c-fos and c-jun mRNA expressions, and AP-1 DNA binding . . . ," *Eur. Neuropsychopharmacol.*, vol. 7:181-187, 1997.

Schreiber et al., "Rapid detection of octamer binding proteins with 'mini-extracts' prepared from a small number of cells," *Nucleic Acids Res.*, vol. 17(15):6419, 1989.

Johnson et al., "Human trabecular meshwork organ culture: A new method," Invest Ophthalmol & Vis Sci., vol. 28(6): 945-953, 1987.

Erickson-Lamy et al., "Outflow facility studies in the perfused human ocular anterior segment," Exp. Eye Res., vol. 52:723-731, 1991.

Clark et al., "Dexamethasone-induced ocular hypertension in perfusion cultured human eyes," *Invest. Ophthalmol. Vis. Sci.*, vol. 36(2):478-489, 1995.

Weiner, A.L., "Polymeric Drug Delivery Systems For the Eye," *Polymeric Site-specific Pharmacotherapy*, Ed., A.J. Domb, John Wiley & Sons, pp. 315-346, 1994.

* cited by examiner

*Primary Examiner*—Zohreh Fay
(74) *Attorney, Agent, or Firm*—Teresa J. Schultz; Sally S. Yeager

(57) ABSTRACT

Compositions comprising AP-1 activators and methods of use for treating glaucoma and ocular hypertension are disclosed.

3 Claims, 1 Drawing Sheet

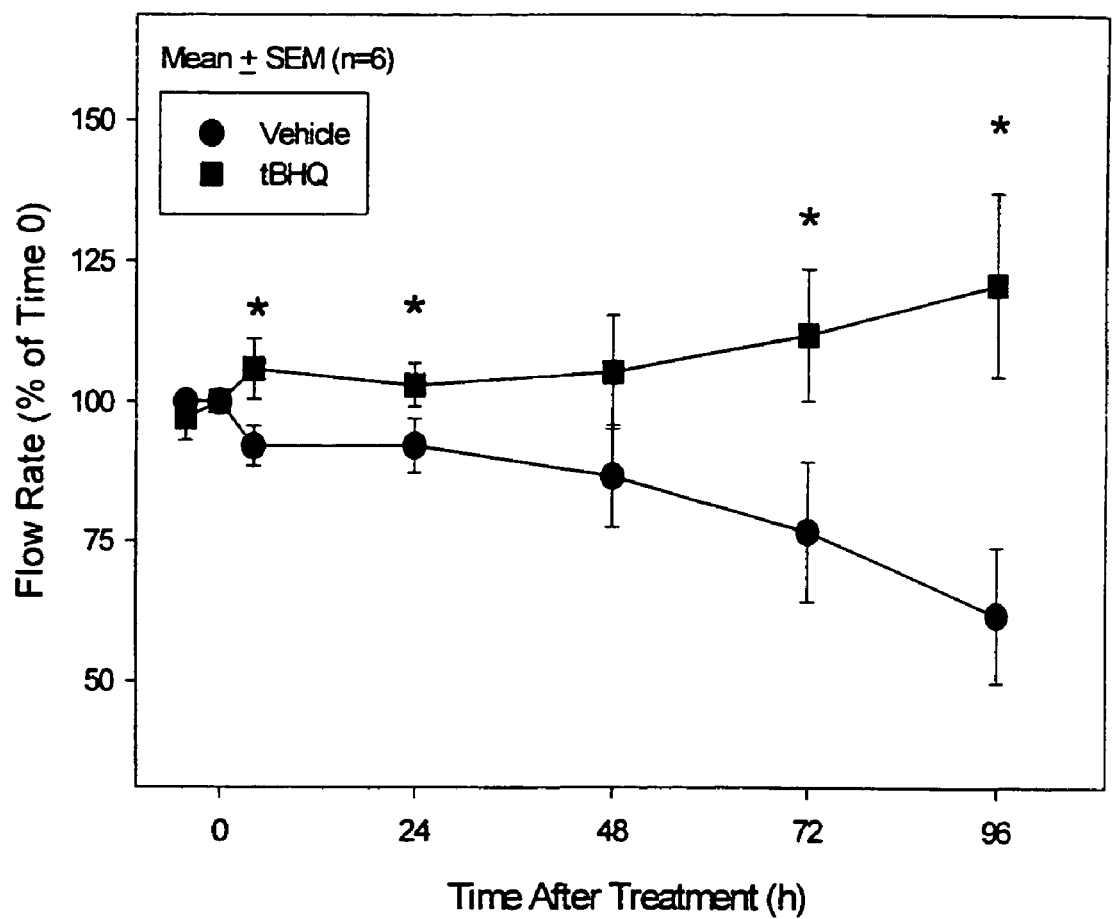

USE OF AP-1 ACTIVATORS TO TREAT GLAUCOMA AND OCULAR HYPERTENSION

This application claims the benefit of Provisional Application No. 60/130,133, filed Apr. 20, 1999.

The present invention relates to the treatment of glaucoma and ocular hypertension. In particular, the present invention relates to the use of compounds that increase the activity of Activator Protein-1 (AP-1) to treat glaucoma and ocular hypertension.

BACKGROUND OF THE INVENTION

Glaucoma is a progressive disease which leads to optic nerve damage and, ultimately, total loss of vision. The causes of this disease have been the subject of extensive studies for many years, but are still not fully understood. The principal symptom of, and/or risk factor for, the disease is elevated intraocular pressure (IOP) or ocular hypertension.

The reasons why IOP is increased in glaucoma patients are not fully understood. It is known that elevated IOP can be at least partially controlled by administering drugs which either reduce the production of aqueous humor within the eye, such as beta-blockers and carbonic anhydrase inhibitors, or increase the flow of aqueous humor out of the eye, such as cholinergic agonists and sympathomimetics.

All types of drugs currently being used to treat glaucoma have potentially serious side effects. Cholinergic agonists such as pilocarpine can cause blurring of vision and other ocular side effects, which may lead either to decreased patient compliance or to termination of therapy. Systemically administered carbonic anhydrase inhibitors can also cause serious side effects, such as nausea, dyspepsia, fatigue, and metabolic acidosis which can affect patient compliance and/or necessitate the withdrawal of treatment. Moreover, some beta-blockers have been known to be associated with pulmonary side effects attributable to their effects on beta-2 receptors in the pulmonary tissue. Sympathomimetics cause tachycardia, arrhythmia and hypertension. There is therefore a continuing need for new therapies which control elevated IOP associated with glaucoma.

Activator protein-1 (AP-1) is a dimeric gene transcription promoter comprised of subunit proteins which are the products of at least three different proto-oncogene families: the Jun (c-Jun, v-Jun, JunB, JunD), Fos (c-Fos, v-Fos, FosB, FosB2, Fra-1, Fra-2) or activating transcription factor (B-ATF, ATF2, ATF3/LRF1) families. Uncomplexed monomers and homo- and hetero-dimers of these protein subunits have been observed in a variety of mammalian and non-mammalian tissues (Foletta et al., *Transcriptional regulation in the immune systems: all roads lead to AP-1, J. Leukoc Biol.* volume 63, pages 139–152 (1998); and Karin et al., *AP-1 function and regulation, Curr. Opin. Cell Biol.*, volume 9, pages 240–246 (1997)).

AP-1 binds to specific DNA sequences within enhancer regions of many genes (e.g., TPA (12-O-tetradecanoylphorbol-13-acetate) response elements (TREs) or cyclic AMP response elements (CREs)) and promotes the activation of the particular gene. Examples of genes which contain AP-1 consensus seqences in their enhancer regions include the genes for SV40 and human metallothionein IIA (Lee et al., *Activation of transcription by two factors that bind promoter and enhancer sequences of the human metallothionein gene and SV40, Nature*, volume 325, pages 368–372). The binding affinity of AP-1 for the various response elements appears to depend on the specific protein subunit dimer complex. Dimers composed of Jun/Jun or Jun/Fos generally bind TREs, whereas ATF/ATF or Jun/ATF dimers preferentially bind CREs (Whitmarsh et al., *Transcription factor AP-1 regulation by mitogen-activated protein kinase signal transduction pathways, J. Mol. Med.*, volume 74, pages 589–607 (1996); and Karin et al., *Current Opin. Cell Biol.*, volume 9, pages 240–246 (1997)). The biological consequences of AP-1 mediated gene transcription may also vary, depending upon the dimer composition. For example, induction of murine glutathione-S-transferase genes is apparently mediated by a Fos/Jun heterodimer which binds at least one TRE sequence within the gene's antioxidant response element (Ainbinder et al., *Regulatory mechanisms involved in activator-protein-1 (AP-1)-mediated activation of glutathione-S-transferase gene expression by chemical agents, Eur. J. Biochem.*, volume 243, pages 49–57 (1997); Xie et al., *ARE-and TRE-mediated regulation of gene expression, J. Biol. Chem.*, volume 270, pages 6894–6900 (1995)), and a c-Jun/ATF-2 complex has been shown to bind to a CRE involved in activation of the T-cell gene for tumor necrosis factor-alpha (Foletta et al., *J. Leukoc. Biol.*, volume 63, pages 139–152 (1998)).

Several AP-1 Activators have been reported previously, including β-naphthoflavone and tert-butylhydroquinone (tBHQ) (Ainbinder et al., *Eur. J. Biochem.*, volume 243, pages 49–57 (1997); Ainbinder et al., *Signaling pathways in the induction of c-fos and c-jun proto-oncogenes by 3-methylcholanthrene, Receptors and Signal Transduction*, volume 7, pages 279–289 (1998); and Oazki et al., *The comparative effects of haloperidol, (−)-sulpiride, and SCH23390 on c-fos and c-jun mRNA expressions, and AP-1 DNA binding activity, Eur. Neuropsychopharmacol.*, volume 7, pages 181–187 (1997)). Nowhere in the art, however, has it been taught or suggested that AP-1 activators may be useful in treating glaucoma or ocular hypertension.

SUMMARY OF THE INVENTION

The present invention is directed to compositions and methods of use for the treatment of glaucoma and ocular hypertension. More specifically, the invention is directed to compositions comprising AP-1 activators and methods of use.

Preferred methods involve the topical administration of compositions comprising tBHQ.

DESCRIPTION OF THE DRAWING

FIG. 1 is a graph showing the effects of tBHQ on IOP in a human ocular perfusion organ culture model.

DETAILED DESCRIPTION OF THE INVENTION

The present invention is directed to compositions and methods of use for the treatment of glaucoma and ocular hypertension.

The compounds useful in the present invention compositions and methods are AP-1 Activators. While not intending to be bound by any theory, it is believed that the stimulation of AP-1 activity leads to the transcription of mRNAs and corresponding translation of proteins useful in effecting the maintenance or lowering of IOP. As used herein, "AP-1 Activator" refers to those molecules which lower IOP via AP-1 mediated transcription. Such activators may include agents which (1) increase the formation and expression of proteins comprising AP-1 complex(es), (2) enhance the formation of such complexes, or (3) promote binding of an AP-1 complex to regulatory/promoter sites on cellular genes. Examples of AP-1 Activators include β-naphthoflavone, tert-butylhydroquinone (tBHQ), sulpiride, haloperidol, and 3-methylcholanthrene. The most preferred AP-1 Activator is tBHQ.

Other AP-1 Activators may be elucidated by methods known in the art. For example, an increase in the level of DNA-bound AP-1 complex, as assessed by electrophoretic mobility shift assay, is an accepted means for detection of activated AP-1 activity. Such DNA-binding can be determined by the following protocol:

DNA-Binding Assay:

Target cellular tissue (e.g., human trabecular meshwork tissue and/or cultured cells) is treated with or without an AP-1 Activator candidate(s). Nuclear extracts of the cells are then prepared according to the method of Schreiber et al., *Rapid detection of octamer binding proteins with 'mini-extracts' prepared from a small number of cells, Nucleic Acids Res.*, volume 17, page 6419 (1989). Electrophoretic mobility shift assays are then carried out with the nuclear extracts as described by Ainbinder et al., *Regulatory mechanisms involved in activator-protein-1 (AP-1)-mediated activation of glutathione-S-transferase gene expression by chemical agents, Eur. J. Biochem.*, volume 243, pages 49–57 (1997). Briefly, extracts are incubated with a $^{32}$P-labelled AP-1 oligonucleotide probe and the resulting complexes are then separated by non-denaturing acrylamide gel electrophoresis. Levels of DNA binding activity can then be determined from analysis of autoradiograms of the dried gels. By using this method, compounds such as tBHQ have been demonstrated to be AP-1 Activators.

Other AP-1 Activators may be identified by routine methods known in the art. For example, methods disclosed in the following publications may be useful in elucidating other AP-1 Activators of the present invention:

(1) Ainbinder et al., *Regulatory mechanisms involved in activator-protein-1 (AP-1)-mediated activation of glutathione-S-transferase gene expression by chemical agents, Eur. J. Biochem.*, volume 243, pages 49–57 (1997);

(2) Ainbinder et al., *Signaling pathways in the induction of c-fos and c-jun proto-oncogenes by 3-methylcholanthrene, Receptors and Signal Transduction*, volume 7, pages 279–289 (1998);

(3) Ozaki et al., *The comparative effects of haloperidol, (−)-sulpiride, and SCH23390 on c-fos and c-jun mRNA expressions, and AP-1 DNA binding activity, Eur. Neuropsychopharmacol.*, volume 7, pages 181–187 (1997); and (4) Xie et al., *ARE-and TRE-mediated regulation of gene expression, J. Biol. Chem.*, volume 270, pages 6894–6900 (1995); the foregoing publications are incorporated herein by reference.

EXAMPLE 1

The following example illustrates the effect of an AP-1 Activator, tBHQ, on aqueous outflow facility as demonstrated using a human ocular perfusion organ culture model. Pharmaceutical candidates which maintain or increase outflow facility are believed to be useful in treating or controlling IOP and, hence, glaucoma. The study was performed as follows:

Human donor eyes less than 24 hours post mortem were used. The globe was sectioned equatorially followed by the removal of vitreous, lens, zonules, iris, and most of the ciliary body. The anterior segment was then mounted on a perfusion dish, perfused with cell culture medium at a constant hydrostatic pressure of 10 mm Hg (Johnson et al., *Human trabecular meshwork organ culture: A new method, Invest Ophthalmol Vis Sci.*, volume 28, pages 945–953 (1987); Erickson-Lamy et al., *Outflow facility studies in the perfused human ocular anterior segment, Exp. Eye Res.*, volume 52, pages 723–731 (1991); and Clark et al., *Dexamethasone-induced ocular hypertension in perfusion cultured human eyes, Invest. Ophthalmol. Vis. Sci.*, volume 36, pages 478–489 (1995)). The flow rate of the perfusate was measured by weighing the reservoir at predetermined periods. After 2 to 4 days of equilibrium period, one eye of each of the donor pair was perfused with the test compound, t-BHQ (10 μM), while the other was perfused with vehicle (control). The results are shown in FIG. 1 and Table 1, below:

TABLE 1

Effect of t-BHQ (10 μM) on Aqueous Outflow Rate in Human Ocular Perfusion Organ Culture

| Time after Treatment | Flow Rate (% of Time 0) (Mean ± SEM, n = 6) | |
| --- | --- | --- |
| (Hours) | Vehicle | t-BHQ |
| −4 | 100.0 ± 0.8 | 97.0 ± 4.0 |
| 0 | 100.0 | 100.0 |
| 4 | 92.0 ± 3.6 | 105.8 ± 5.4* |
| 24 | 92.0 ± 4.8 | 102.9 ± 3.9* |
| 48 | 86.6 ± 9.2 | 105.2 ± 10.1 |
| 72 | 76.6 ± 12.5 | 111.8 ± 11.8* |
| 96 | 61.8 ± 12.1 | 120.9 ± 16.4* |

Note: (1) The basal flow rate at time 0 for vehicle-treated eyes was 3.55 ± 1.00 μL/min, and that for drug-treated eyes was 4.09 ± 0.63 μL/min.
(2) *represents $p < 0.05$, paired t-test compared to the vehicle-treated eye of the same time point.

While not intending to be bound by any theory, it is believed that the AP-1 Activators of the present invention are useful in increasing the outflow facility of a mammal's eye, which leads to maintained or lowered IOP, and thus useful in the treatment of glaucoma or ocular hypertension.

The preferred route of administration for the methods of the present invention is topical. The preparation of topical ophthalmic compositions is well known in the art. Generally, topical ophthalmic compositions useful in the present invention will be in the form of a solution, suspension, gel, or formulated as part of a device, such as a collagen shield or other bioerodible or non-bioerodible device. Various excipients may be contained in the topical ophthalmic solutions, suspensions or gels of the present invention. For example, buffers (e.g., borate, carbonate, phosphate), tonicity agents (e.g., sodium chloride, potassium chloride, polyols), preservatives (e.g., polyquaterniums, polybiguanides, benzalkonium chloride), chelating agents (e.g., EDTA), viscosity enhancing agents (e.g., polyethoxylated glycols) and solubilizing agents (e.g., polyethoxylated castor oils, including polyoxl-35 castor oil (Cremophor EL®, BASF Corp., Parsippany, N.J.); Polysorbate 20, 60 and 80; Pluronic® F-68, F-84 and P-103 (BASF Corp.); or cyclodextrin) may be included in the topical ophthalmic compositions. However, preferable compositions of the present invention will not include preservatives or tonicity agents which are known to adversely affect or irritate the eye.

A variety of gels may be useful in topical ophthalmic gel compositions of the present invention, including, but not limited to, carbomers, polyvinyl alcohol-borates complexes, or xanthan, gellan, or guar gums. Topical ophthalmic bio-erodible and non-bioerodible devices are known in the art and may be useful in the topical administration of the AP-1 Activators. See, for example, Weiner, A. L., *Polymeric Drug Delivery Systems For the Eye*, in *Polymeric Site-specific Pharmacotherapy*, Ed., A. J. Domb, John Wiley & Sons, pages 316–327 (1994). While the particular ingredients and amounts to be contained in topical ophthalmic compositions useful in the methods of the present invention will vary, particular topical ophthalmic compositions will be formulated to effect the administration of one or more AP-1 Activators topically to the eye.

In general, the doses of AP-1 Activators used for the above described purposes will vary, but will be in an amount effective to maintain or lower IOP, or otherwise treat glaucoma or ocular hypertension. As used herein, the term "pharmaceutically effective amount" refers to that amount of an AP-1 Activator administered to a mammal which maintains or lowers IOP, or otherwise ameliorates the glaucomatous condition of the patient. The AP-1 Activators will normally be contained in the compositions described herein in an amount from about 0.00001 to about 2.0 percent weight/volume ("% w/v"), preferably 0.01 to 2% w/v. The compositions of the present invention may be delivered topically to the eye, about one to six times a day.

As used herein, the term "pharmaceutically acceptable vehicle" refers to any formulation which is safe, and provides the appropriate delivery for the desired route of administration of an effective amount of at least one AP-1 Activator of the present invention.

Preferred formulations of AP-1 Activators combinations of the present invention include the following Examples 2–3:

EXAMPLE 2

Topical Ophthalmic Formulation:

| Ingredient | Amount (% wt) |
| --- | --- |
| AP-1 Activator | 0.01 to 2 |
| Phosphate Buffered Saline | 1.0 |
| Benzalkonium Chloride | 0.01 |
| Polysorbate 80 | 0.5 |
| Purified water | q.s. to 100% |

EXAMPLE 3

Topical Ophthalmic Formulation:

| Ingredient | Amount (% wt) |
| --- | --- |
| t-HBQ | 0.01 to 2 |
| Phosphate Buffered Saline | 1.0 |
| Hydroxypropyl-β-cyclodextrin | 4.0 |
| Purified water | q.s. to 100% |

EXAMPLE 4

Preferred Formulation for a Topical Ophthalmic Solution:

| Component | Amount (% wt) |
| --- | --- |
| t-HBQ | 0.01 to 2 |
| Benzalkonium chloride | 0.01 |
| HPMC | 0.5 |
| Sodium chloride | 0.8 |
| Sodium phosphate | 0.28 |
| Edetate disodium | 0.01 |
| NaOH/HCl | q.s. to pH 7.2 |
| Purified Water | q.s. to 100% |

We claim:

1. A method for treating glaucoma or ocular hypertension which comprises administering to a mammal a composition comprising an AP-1 Activator selected from the group consisting of β-naphthoflavone, 3-methylcholanthrene, and tert-butylhydroquinone, and a pharmaceutically acceptable vehicle.

2. A method according to claim 1, wherein the AP-1 Activator is tert-butylhydroquinone.

3. A method according to claim 1, wherein the composition comprises:
   about 0.01 to 2.0% w/v t-BHQ
   about 0.28% w/v sodium phosphate;
   about 0.8% w/v sodium chloride;
   about 0.01% w/v benzalkonium chloride
   about 0.5% w/v HPMC
   about 0.1% w/v edetate disodium; and water.

* * * * *